United States Patent
Hawkes

(10) Patent No.: US 7,723,576 B2
(45) Date of Patent: May 25, 2010

(54) METHOD OF SELECTIVELY PRODUCING MALE OR FEMALE STERILE PLANTS

(75) Inventor: Timothy Robert Hawkes, Bracknell (GB)

(73) Assignee: Syngenta Limited (GB)

( * ) Notice: Subject to any disclaimer, the term of this patent is extended or adjusted under 35 U.S.C. 154(b) by 957 days.

(21) Appl. No.: 10/564,050

(22) PCT Filed: Jun. 9, 2004

(86) PCT No.: PCT/GB2004/002453

§ 371 (c)(1),
(2), (4) Date: Aug. 11, 2006

(87) PCT Pub. No.: WO2005/005642

PCT Pub. Date: Jan. 20, 2005

(65) Prior Publication Data

US 2007/0044169 A1    Feb. 22, 2007

(30) Foreign Application Priority Data

Jul. 10, 2003   (GB)   ................. 0316190.8

(51) Int. Cl.
*C12N 15/82*   (2006.01)
*C12N 15/54*   (2006.01)
*C12N 15/55*   (2006.01)
*A01H 1/02*    (2006.01)

(52) U.S. Cl. ........... 800/303; 800/274; 800/278; 800/287; 800/300; 435/193; 435/195

(58) Field of Classification Search ............. None
See application file for complete search history.

(56) References Cited

U.S. PATENT DOCUMENTS

| 4,922,013 | A | * | 5/1990 | Schutze et al. | ............... 562/15 |
| 5,356,799 | A | * | 10/1994 | Fabijanski et al. | .......... 800/274 |
| 5,463,175 | A | * | 10/1995 | Barry et al. | ................ 800/300 |
| 5,977,433 | A | * | 11/1999 | Williams et al. | ............ 800/274 |
| 6,384,304 | B1 | * | 5/2002 | Quandt et al. | ............ 800/320.3 |
| 6,555,733 | B2 | * | 4/2003 | Bartsch et al. | ............... 800/288 |

OTHER PUBLICATIONS

McCabe et al. Theoretical and Applied Genetics 99(3-4): 587-592 (Aug. 1999).*
Droge-Laser et al. Plant Physiology 105: 159-166 (1994).*

* cited by examiner

*Primary Examiner*—David T Fox
(74) *Attorney, Agent, or Firm*—S. Matthew Edwards

(57) ABSTRACT

A method of producing male or female sterile plants comprising providing means for inactivating a herbicide and means for reactivating the thus inactivated herbicide, wherein the herbicide inactivating means is provided within vegetative tissues and the reactivating means is provided in either the male or female reproductive structures of the plant, so that the vegetative, but not reproductive, structures are protected from the phtyotoxic activity of the herbicide when applied to the plant.

4 Claims, 1 Drawing Sheet

SEQUENCE LISTING

<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1
aactgcagct ttttggttag cgaatgc                                      27

<210> SEQ ID NO 2

```
<211> LENGTH: 35
<212> TYPE: DNA
<213> ORGANISM: Artificial Sequence
<220> FEATURE:
<223> OTHER INFORMATION: Primer

<400> SEQUENCE: 2
cagactagtt ttagctaatt tctttaagta aaaac                              35
```

METHOD OF SELECTIVELY PRODUCING MALE OR FEMALE STERILE PLANTS

Figure 1:
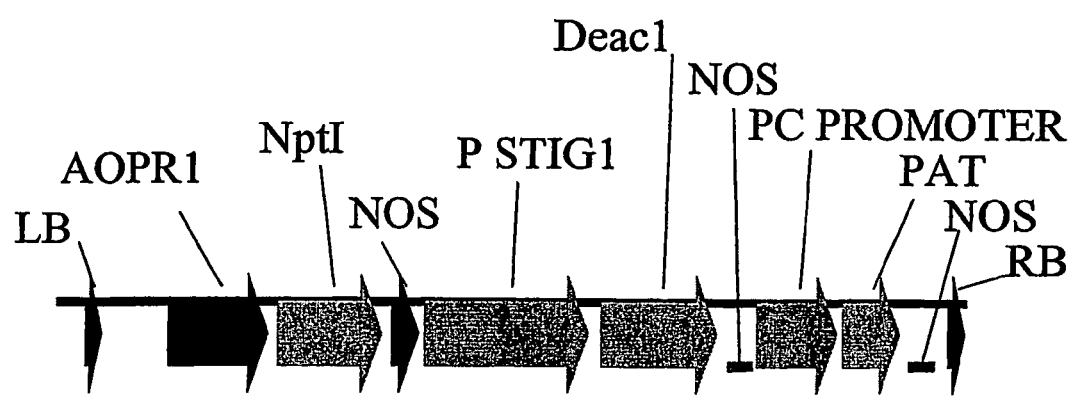

This application claims foreign priority benefits under 35 U.S.C. §119 and/or §365 of Great Britain application GB 0316190.8, filing date Jul. 10, 2003. This application also claims priority benefit under 35 U.S.C. §120 and/or §363, and/or §365 for PCT international application PCT/GB20041002453, filing date Jun. 9, 2004.

BACKGROUND

Heterosis in crop plants can have a marked effect on yield improvement. In general, hybrids exhibit increased yields in comparison with non-hybrid varieties. Hybrids usually give a greater return unit for growth factors such as water and fertilizer. Hybrids often offer superior stress tolerance, uniformity in product and maturity and also afford a simple breeding opportunity to combine characteristics or traits that may be difficult to combine in other ways. Hybrid vigour in plants is generally of sufficient magnitude to warrant commercial exploitation. Commercial hybrids are used extensively in many crops including corn, sorghum, sugar beet, sunflower and canola. However, owing mainly to the lack of economical hybrid seed production methods, wheat, barley and rice are still grown mainly as inbreds.

Traditionally, hybrid seed production involves planting out separate blocks of female and male parent lines with only the seed from the female parents being harvested. To ensure that this seed is hybrid, self pollination of the female parent line must be minimised by rendering the line male-sterile. Methods for making the female parent line male sterile include mechanical, chemical and genetic methods. In monoecious plants, such as maize, male sterility can be readily achieved mechanically by detasselling of the male infloresence. However most crops are diecious and having male and female organs within the same flower makes such physical emasculation impractical. Genetic approaches have therefore sometimes been used.

Genetic male sterility traits which occur are normally controlled by nuclear genes in which the alleles associated with the sterile phenotype are generally expressed recessively with respect to the corresponding alleles associated with fertility. Where genetic male sterility occurs it is normally associated with a single recessive gene that must be homozygous in order for male sterility to be expressed. In order to make practical use of such genetic male sterility traits, breeders usually develop a phenotypically uniform female line that segregates into male-sterile and male-fertile plants. The male fertile plants, once identified, need to be rogued out which is labour intensive. There is always a problem with maintaining the parental line since male fertile plants cannot be eliminated from the population because they are essential for maintenance of the population. Rather than rely on the existence of natural male sterility alleles it is also possible to use molecular biological methods. Plants may be engineered which express, for example, anti-sense or ribozyme genes that decrease or eliminate expression of key genes necessary for the formation of viable pollen. Such transgenic lines of plants are male-sterile and are used for the production of hybrid seed by crossing using pollen from male-fertile plants. The main problem with such lines is that they can only be maintained in a heterozygous state in subsequent generations, via crosses with the isogenic fertile lines. This can be a problem in hybrid seed production where yield is critical. Although, for example by linking herbicide resistance to male sterility, it may be possible to selectively rogue out the male-fertile plants this still necessitates that the plants are planted initially at extra high densities.

The use of cytoplasmic male sterility for commercial hybrid production requires a stable male-sterile cytoplasm and a source of pollen. The cytoplasmic-genetic system of male sterility requires the existence of three types of line for hybrid production, the A line (cytoplasmic male-sterile), B line (male-fertile maintainer) and R line (male fertile with restorer genes). Three-way crosses produced with this system involve maintenance and production of four lines, an A and a B line of one inbred and male-fertile inbreds of the other two. Reliance on a single source of male-sterile cytoplasm can minimise breeding flexibility and lead to progeny with wholesale susceptibility to particular diseases.

Hybrid seed can also be produced through the use of chemicals that inhibit viable pollen formation. These chemicals, called gametocides, are used to impart transitory male-sterility. However the expense, registerability and reliability of gametocides has limited their use.

A shortcoming of traditional hybrid seed production systems is the need to plant separate rows or blocks of the male and female parent lines. Here low efficiency pollination is an especially acute problem in crop species, such as wheat, that release small amounts of pollen which does not travel far on the wind. In such crops as much as two/thirds of the hybrid-producing field needs to be dedicated to male pollen-donor plants and then hybrid seed production therefore becomes uneconomic.

In order to achieve more economic seed production in wheat and other crops it is necessary to move male and female plants closer together for more efficient pollen transfer; most efficiently by interplanting males and females within centimeters of each other in the same rows. In such a system it would be impractical to harvest only the seed from the (male-sterile) female parents. The contamination with non-hybrid seed originating from the male parent can be minimised by using as low a percentage of such male parent plants in the planting mix as possible and/or by using male plants which are female sterile. A method for constructing a dominant female sterile line has been described (EP 412,006 A1 (1990); Goldman et al., (1994) EMBO. J., 13, 2976-2984) but, as with the male sterile lines, the line has to be maintained as a heterozygote.

Accordingly there remains a need for simple economic methods of hybrid seed production. In particular, in order efficiently to produce hybrid seed there remains a need to provide both male-sterile female parental lines and female-sterile male parental lines which can be easily maintained as pure homozygous lines and which are useful for efficient hybrid seed production. Methods which are described in the art for achieving this include methods wherein hybrid seed is produced from male and female parent lines at least one of which comprises a heterologous chimeric gene, preferentially expressed in floral tissue, which renders the line conditionally sterile dependent upon the exogenous application of a non-phytotoxic substance which can be specifically and locally converted to a phytotoxin by an enzyme which is encoded by the heterologous chimeric gene and which is preferentially expressed in either the male or female reproductive structures. The non-phytotoxic substance may be a pro-herbicide. The advantage of having such conditionally sterile parent lines is that it allows them to be maintained as homozygotes with respect to the sterility trait. Fertility is only disrupted upon exogenous application of the non-phytotoxic substance. In one such example of a conditional male sterility system a gene encoding a deacetylase enzyme (see for example U.S. Pat. No. 6,555,733) is preferentially expressed in tapetal cells of male flower tissue where it converts the exogenously applied pro-herbicide, N-acetyl L phosphinothricin, to the phytotoxin L phosphinothricin and thus prevents viable pollen formation; or alternatively the enzyme is expressed in stigma cells and application of pro-herbicide N-acetyl L phosphinothricin thus prevents viable seed formation. In further similar examples: (i) tapetum preferential expression of a bacterial cytochrome P450 catalyses conversion of pro-herbicide R7402 to a sulphonylurea phytoxin which prevents the production of viable pollen; and (ii) tapetum preferential expression of a phosphonate monoester hydrolase catalyses conversion of glyceryl glyphosate pro-herbicide to the phytotoxin glyphosate which also prevents production of viable pollen. WO 98/03838 describes examples of a conditional female sterility system wherein enzymes capable of converting the pro-herbicides to phytoxins are preferentially expressed in female reproductive structures.

Despite the existence of these methods for making male and female parent lines that are conditionally sterile, hybrid seed production remains far from routine in crops such as wheat. The current inventions concern, inter alia, improvements in the art with respect to the generation of female parent lines which are conditionally male sterile and male parent lines which are conditionally female sterile.

Chemical hybridising agents and pro-herbicides are expensive since they are not manufactured on a large scale. It would be desirable to, instead, use a relatively cheap ready-registered substance such as a commercial herbicide as a chemical hybridising agent. This would also achieve further efficiency since weed control could be combined with chemical hybridisation in a single spray application.

SUMMARY

According to the present invention there is provided a method of producing male or female sterile plants comprising providing means for inactivating a herbicide and means for reactivating the thus inactivated herbicide, wherein the herbicide inactivating means is provided within vegetative tissues and the reactivating means is provided in either the male or female reproductive structures of the plant, so that the vegetative, but not reproductive, structures are protected from the phytotoxic activity of the herbicide when applied to the plant. The means may be any wherein the means is an enzyme. A preferred embodiment of the present inventive method comprises the steps of transforming plant material with a polynucleotide which encodes a first enzyme which is capable of N-acetylating L-phosphinothricin and a second enzyme which is capable of hydrolyzing, or otherwise removing the acetyl group from, the N-acetyl L-phosphinothricin to yield L-phosphinothricin, and regenerating the thus transformed material into a plant, wherein the first enzyme is expressed only in the green tissues of the plant and wherein L phosphinothricin herbicide is applied to the plant foliarly up to the time of male or female gamete formation and/or maturation, so that the plant is substantially undamaged by the application of herbicide and wherein the second enzyme is expressed preferentially in either male or female reproductive structures so that the selective local regeneration of L phosphinothricin in these tissues prevents the formation of the said gametes, or otherwise renders them non-functional.

As indicated above, in a preferred method the herbicide is L phosphinothricin, the non-phytotoxic substance is N-acetyl L phosphinothricin, the inactivating enzyme is a phosphinothricin N-acetyl transferase (PAT) and the activating enzyme is any amidase capable of hydrolyzing N-acetyl L phoshinothricin (e.g the arg E gene product, U.S. Pat. No. 6,555,733 etc). In a further preferred embodiment the PAT enzyme is expressed under operable control of a plastocyanin promoter region. Accordingly, the current invention provides a method of using a relatively cheap commercial herbicide as both the hybridisation agent and, at the same time, to provide weed control in the hybrid seed production field and to therefore improve the efficiency and yield of the hybrid crop.

Even given the above provision of the current invention there remains a further problem to overcome in respect of the use of the said herbicide as a means of weed control in F1 generation of plants that result from the hybrid seed provided by the foregoing method. This generation of the crop contains at least two genes (one from each parent) encoding herbicide inactivating enzymes and capable of providing tolerance to the herbicide. It would be desirable that the said herbicide could also be used for selective weed control in the F1 crop. However, owing to the presence of the two florally-expressed genes which encoding activating enzyme, the F1 crop would display vegetative tolerance to the herbicide but little or reduced grain yield following application of the said herbicide to the crop.

Thus, in a further provision of the current invention, there is provided a further method, wherein the inactivating enzyme is additionally expressed from a floral promoter so that it is expressed substantially only in green tissues and in reproductive tissues other than those reproductive tissues in which the gametes are rendered non-functional. In the hybrid crop, this co-expression of the inactivating enzyme in the floral tissue counterbalances the effect of the activating enzyme and therefore prevents loss of yield upon application of herbicide. The current invention therefore provides a method of overcoming the problem of enabling the use of a cheap commercial herbicide, phosphinothricin, as both weed control and hybridising agent in the production of, for example, hybrid cereals and which method, furthermore, provides resultant hybrid F1 crops of cereals or rice in which phosphinothricin (or L phosphinothricin) can be safely used for weed control without substantial loss of yield. As a yet further benefit, F2 plants arising from selfed seed of the F1 generation which may later arise as volunteers in subsequent crops will be easier to manage since they, themselves, will generally be sterile (or of substantially reduced fecundity) if sprayed with controlling amounts of phosphinothricin. The same will hold for the progeny of pollen outcrossing from the F1 plants to weeds (e.g red rice) or other cereals In one embodiment, the current invention provides a method wherein female and male parental lines are interplanted together in suitable ratios in a field and sprayed with phosphinothricin at a suitable rate between 0.05 and 10 kg/ha and at suitable timings so as to optimise the production of hybrid seed. Optionally, the hybrid seed thus produced give rise to F1 progeny both vegetatively and reproductively tolerant to application of the herbicide phosphinothricin which herbicide may thus be used for weed control. Such hybrid seed also have the advantage that the herbicide tolerance trait that they express will be only incompletely passed onto future selfed generations or outcrossed into related weeds.

The current invention relates to improvements in methods for the production of crop hybrid seed. In particular the invention relates to a method of hybrid seed production from male and female parent lines which are conditionally female or male sterile dependent upon the exogenous application of a herbicide and wherein both lines are substantially vegetatively tolerant to the said herbicide and wherein the herbicide is applied at a time and in sufficient amount that self fertilization is minimised or prevented. The current invention also relates to a method of generating conditionally male or female-sterile plants by i) transforming plant material with one or more chimeric genes which encode an inactivating enzyme capable of converting herbicide to a non-phytotoxic substance and an activating enzyme capable of transforming the said non-phytotoxic substance to herbicide. The activating enzyme is expressed under operable control of one or more promoters which, in the case of conditionally male sterile plants, causes the enzyme to be expressed substantially only in the male reproductive structures or which, in the case of conditionally female sterile plants, causes the said enzyme to be expressed substantially only in the female reproductive structures. The inactivating enzyme is expressed under operable control of a promoter region which leads to expression substantially only in the green tissues or, optionally, is under operable control of two or more promoter regions such that the inactivating enzyme is additionally expressed from a floral promoter so that it is expressed substantially only in green tissues and in reproductive tissues other than those reproductive tissues in which the gametes are rendered non-functional. The plant material is regenerated into morphologically normal fertile plants which are conditionally male or female sterile. The invention also includes the use of conditionally male-sterile plants in combination with conditionally female-sterile plants to produce more efficiently hybrid seed, the use of phosphinothricin as a hybridising agent, certain chimeric genes and the use of these chimeric genes to produce hybrid seeds. The invention also provides conditionally male-sterile, conditionally female-sterile plants, seeds of these plants and hybrid seeds produced by the method. In preferred embodiments of the invention the crop plants to which the method for making hybrid seed is applied are maize, rice, sorghum, wheat, millet, oats, canola and barley.

Nomenclature: Definitions

'deacetylase' or 'amidase' as used herein refers to any enzyme capable of hydrolysing N-acetyl L phosphiniothricin 'Gene' as used herein refers to any DNA sequence comprising several operably linked DNA fragments such as a promoter and a 5' regulatory region, a coding sequence and an untranslated 3' region comprising a polyadenylation site.

'Chimeric' when referring to a gene or DNA sequence is used to refer to the fact that in nature, the coding sequence is not associated with the promoter or with at least one other regulatory region of the DNA in the gene.

'Chimeric gene' as used herein refers to a gene wherein, in nature, the coding sequence is not associated with the promoter or with at least one other regulatory region of the DNA in the gene.

'Expression cassette' as used herein refers to a transferable region of DNA comprising a chimeric gene which is flanked by one or more restriction or other sites which facilitate precise excision from one DNA locus and insertion into another.

'Non-phytotoxic substances' are, in the context of the current invention, substances which are relatively non-phytotoxic to plants, cells or tissues of any particular crop to which the method of the invention is applied. Non-phytotoxic substances need not be non-phytotoxic in all plant tissues of all plants.

'Female reproductive structure' means the female gametes and those portions of the plant that are specialised for the production, maturation and viability of female gametes. Normally this comprises those portions of a plant that comprise the carpel or gynoecium ("pistill"). The carpel of a plant includes but is not limited to a stigma, style, ovary and cells or tissues that are comprised by the stigma, style and ovary.

'Male reproductive structure' means the male gametes and those portions of the plant that are specialised for the production, maturation and viability of male gametes. This comprises those portions of a plant that comprise, for example, microspores, stamens, tapetum, anthers and the pollen.

'Female-sterile plant' as used herein is a plant that is incapable of supporting viable seed formation when pollinated with functional or viable pollen. Such female sterility can be the result of breeding selection or the presence of a transgene. A 'conditionally female-sterile plant' refers to a plant which under normal growing conditions is female fertile and which can become female-sterile under specific conditions. In the context of the current invention such a 'female-sterile plant' or 'conditionally female-sterile plant' remains male fertile and able to produce viable pollen.

'Male-sterile plant' as used herein is a plant that is incapable of supporting viable pollen formation. Such male sterility can be the result of breeding selection or the presence of a transgene. A 'conditionally male-sterile plant' refers to a plant which under normal growing conditions is male fertile and which can become male-sterile under specific conditions. For example the conditions might comprise physical emasculation or application of a specific chemical gametocide. In the context of the current invention such a 'male-sterile plant' or 'conditionally male-sterile plant' remains female fertile and able to produce viable seeds when pollinated with functional or viable pollen.

'Promoter region' as used herein is a region of DNA comprising at least a functional promoter and, optionally, some or all of its associated upstream regulatory sequences including enhancer sequences- and/or associated downstream sequences including some or all of the 5' untranslated region of the gene endogenous to the promoter.

'Inter-planting' as used herein refers to a method of planting seeds or plants in a field that ensures adequate cross-pollination of male sterile or conditionally male-sterile plants by the male-fertile plants. This can be achieved either by random mixing of female and male parent seed in different blends (80/20; 90; 10; etc) before planting or by planting in specific field patterns whereby different seeds are alternated. When separate harvesting from different plants is required planting in alternating blocks or rows is preferred.

In the method according to the invention the said herbicide may be applied in mixture along with at least one further substance which may be selected from the group consisting of amino acids, safeners, gametocides, glutathione-5-transferase inducers, cytochrome P450 inducers, fertilizers, herbicides, nematocides, synergists, insecticides, fungicides, hormones, plant-growth regulators and cytochrome P450 inhibitors.

BRIEF DESCRIPTION OF THE FIGS

FIG. 1: A construct comprising the DNA sequence encoding the deacetylase under operable control of the stigl promoter region and also the DNA sequence (A02774) encoding L-phosphinothricin N-acetyl transferase (PAT) under operable control of the pea plastocyanin promoter region is cloned into a site between the LB/npt II gene and the RB of the T-DNA of the binary vector.

DETAILED DESCRIPTION

DNA sequences encoding the enzymes used in the present invention may, optionally, be further mutated and selected in order to generate further useful enzymes having improved utility. Many characteristics of enzymes are thus improved including catalytic activity kcat/Km) versus the desired substrate, temperature stability and pH optimum. Methods for generating, screening and selecting for such improved variants are well known. For example, suitable variant DNA sequences are generated by a process of mutagenesis (e.g by passaging DNA through bacterial or yeast strains with error-prone DNA replication such as *E. coli* XL1 red, by UV, chemical or targeted oligonucleotide PCR mutagenesis). In particular such genes are produced by any of a number of alternative processes of DNA shuffling or 'sexual PCR' as, for example, summarised in WO 0061740 from pages 28-41 all of which are included by reference herein. Many methods are suitable for selecting such improved genes. Genes may be suitably expressed in a suitable host cell such as *E. coli* or yeast and selected for improvement using suitable such assays as, for example, described herein.

The chimeric genes encoding the inactivating enzymes for use in the invention which are capable of converting herbicide to a non-phytotoxic substance may each comprise a DNA sequence which encodes one of said enzymes operably linked to a 5' promoter region which preferentially directs expression to substantially only the green tissue of the plant. This specificity of expression ensures that herbicide inactivation takes place substantially only in the green tissue and therefore that the tissue-killing effect of herbicide locally regenerated from the non-phytotoxic substance via selective expression of activating enzyme within the locality of tissues forming the gametes that it is desired to ablate is not compromised. In addition to promoter regions chimeric genes according to the current invention also comprise a 3' transcriptional terminator sequence. This is responsible for the termination of transcription and correct mRNA polyadenylation. Many such 3' transcriptional terminator sequences are known in the art and are suitable for use in the chimeric genes of the current invention. In particular embodiments the 3' transcriptional terminator sequence is selected from the CMV 35S terminator, the tml terminator, the nopaline synthase (nos) terminator and the pea rbcS E0 terminator. In particular embodiments the herbicide is L-phosphinothricin and the inactivating enzyme is PAT, an enzyme well known in the art as one capable of catalysing the N-acetylation of L phosphinothricin For example suitable PAT enzymes and sequences encoding them are described in EP257542 (*Streptomyces viridichromogenes* PAT enzyme), EP617121, EP297618, EP290986 (Alcaligenes PAT enzyme), EP275957 (optimised *Streptomyces* genes). In further particular embodiments the 5' promoter region which preferentially directs expression to substantially only the green tissue of the plant is or is derived from a plastocyanin gene promoter region and may, for example, be derived from the ~1 kb promoter region 5' of the barley plastocyanin gene (EMBL: Z28347).

The chimeric genes encoding the activating enzymes for use in the invention which are capable of converting the non-phytotoxic substance resulting from the activity of the inactivating enzyme on the herbicide to herbicide, may each comprise a DNA sequence which encodes one of said enzymes operably linked to a 5' promoter region which preferentially directs expression to either the male or the female reproductive structures. This specificity of expression ensures that the effect of the expressed enzyme(s) will be exerted only within the locality of the tissues and cells necessary for formation of viable seed or viable pollen and will not be deleterious to the plant beyond its effect on fertility in the presence of the non phytotoxic substance. In addition to promoter regions chimeric genes according to the current invention also comprise a 3' transcriptional terminator sequence. This is responsible for the termination of transcription and correct mRNA polyadenylation. Many such 3' transcriptional terminator sequences are known in the art and are suitable for use in the chimeric genes of the current invention. In particular embodiments the 3' transcriptional terminator sequence is selected from the CMV 35S terminator, the tml terminator, the nopaline synthase (nos) terminator and the pea rbcS E0 terminator. In particular embodiments the activating enzyme is an amidase capable of hydrolysing N-acetyl-L-phosphinothricin. For example the enzyme is the N-acetyl glutamate deacetylase (deac 1) described in U.S. Pat. No. 6,555,733 (optionally further mutated and selected for improved substrate specificity in respect of N-acetyl phosphinothricin). Alternatively the deacetylase gene may be any one of a number described in the literature and, for example, as described in EP 942965 and in EP 531716 B1.

Further, optional, chimeric genes encoding the inactivating enzymes for use in the invention which are capable of converting herbicide to a non-phytotoxic substance may each comprise a DNA sequence which encodes one of said enzymes operably linked to a 5' promoter region which preferentially directs expression to either the male or the female reproductive structures. The specificity of this expression is chosen to ensure that the effect of the expressed enzyme(s) will be exerted only within the locality of the tissues and cells necessary for the formation of those gametes other than those that it is desired to ablate via localised expression of the activating enzyme. In other words, if the activating enzyme is expressed in the male gamete forming tissue in order to generate a conditionally male sterile plant then the inactivating enzyme is expressed, aside from in the green tissues, only in the female gamete forming tissues. The detailed tissue locality and timing of preferential floral expression of the inactivating enzyme is chosen so that it does not compromise the gamete sterilising effect of the activating enzyme in the conditionally male and sterile parent lines used to generate the hybrid but, nevertheless, does counteract any potential sterilising effects of activating enzyme expression in the F1 hybrid progeny. Ideally, the same 5' promoter region as used to effect the expression of activating enzyme in male floral tissue in the female parent line as is used to drive expression of inactivating enzyme in the female parent line. Similarly, the same 5' promoter region as used to effect the expression of activating enzyme in female floral tissue in the male parent line is used to effect expression of inactivating enzyme in the male parent line. In addition to promoter regions chimeric genes according to the current invention also comprise a 3' transcriptional terminator sequence. This is responsible for the termination of transcription and correct mRNA polyadenylation. Many such 3' transcriptional terminator sequences are known in the art and are suitable for use in the chimeric genes of the current invention. In particular embodiments the 3' transcriptional terminator sequence is selected from the CMV 35S terminator, the tml terminator, the nopaline synthase (nos) terminator and the pea rbcS E0 terminator.

5' Promoter regions suitable for use in certain embodiments of the said chimeric genes include 5' regions of genes which are preferentially expressed in female floral tissues. In certain embodiments the 5' promoter region is selected from the group consisting of the stig 1 promoter of tobacco (Goldman et al., (1994) EMBO J., 13, 2976-2984), a modified S13 promoter (Dzelkalns et al (1993) Plant Cell, 5, 8555), the AGL5 promoter (Savidge et al (1995) Plant Cell, 7, 721-733 and the promoter region 5' of the maize-carpel specific ZAG2 gene (Thiessen et al (1995) Gene, 156, 155-166). Optionally, further suitable promoter regions are obtained from regions upstream of the coding sequences of genomic DNA corresponding to cDNA sequences known in the art to be preferentially expressed in female reproductive structures. In certain embodiments such probe cDNAs are selected from the group consisting of the *Arabidopsis* Fbp7 and Fbp11 genes (Angenent et al., (1995) Plant Cell, 7, 1569-1582) and the orchid-specific cDNAs O40, O108, O39, O126 and O141 (Nadeau et al., (1996) Plant Cell, 8, 213-239). In particular embodiments 5' promoter regions comprising genomic DNA associated with preferential expression in female reproductive structures is selected from DNA regions comprised within the group consisting of the genomic DNA clone pSH64 having the accession number NRRL B-21920, genomic clone, pCIB10302 hybridising to the cDNA P26-A4 having the accession number NRRL B-21655 and genomic DNA clone X2-1 hybridising to cDNA clone P19-QA having the accession number NRRL B-21919. In further particular embodiments these promoter regions comprise nucleotides 1 to 1390 of SEQ ID No. 11, SEQ ID No.2 and nucleotides 1 to 1093 of SEQ ID No. 4 in WO 98/39462. In further embodiments, further 5' promoter regions suitable for use in the chimeric genes of the invention are isolated and cloned by methods which are familiar to one skilled in the art. For example, novel transcripts expressed in female reproductive structures are identified by isolating RNA from tissues such as maize silks or wheat pistils followed by differential screening using techniques such as differential display, PCR select cDNA subtraction and subtractive cDNA library construction. cDNA clones that are preferentially expressed in the female tissues and not in other parts of the plant such as the leaves, roots and tassels. The tissue specificity of expression is, optionally, further confirmed by Northern blotting. The cDNA clones are used as probes for genomic library screening. 5' promoter regions and, optionally, 3' untranslated DNA regions associated with tissue preferential expression are obtained from the genomic DNA clones and used in the construction of chimeric genes for preferential expression in female reproductive structures.

5' Promoter regions suitable for use in certain embodiments of the said chimeric genes include 5' regions of genes which are preferentially expressed in male floral tissues. These include promoter regions for expression in pollen, the tapetum or other structures in the anther. In certain embodiments these 5' promoter regions are selected from the group consisting of the LAT52 promoter (Twell et al., (1989) Dev., 109, 705-713), the tomato A127 promoter (Dotson et al., (1996) Plant J., 10, 383=392), the maize Zmg promoter (Hamilton et. al., (1989) Sex. Plant Reprod. 2, 208-212), the maize CDPK promoter (Guerro et al., (1990) Mol. Gen. Genet., 224, 161-168) and the anther specific ant32 and ant43D promoters disclosed in U.S. Pat. No. 5,477,002 herein incorporated by reference in its entirety. In certain further embodiments the 5' promoter region is selected from the group consisting of the tapetum-specific promoter CA55 from maize ("Pca55" described in WO 92/13956), the tapetum-specific promoter E1 from rice (described in U.S. Pat. No. 5,639,948), the tapetum-specific promoter T72 from rice (described in U.S. Pat. No. 5,639,948), the RA8 anther-specific promoter from rice (EMBI/Genbank accession number AF042275; Jean J s et al, (1999) PMB, 39, 35-44) the anther-specific Tap1 promoter (Spena et al (1992) Theor Appl Genet 84, 520-527) and the ZmC5—pollen specific promoter from maize (EMBL/Genbank accession number Y13285; Wakeley et al, (1998) PMB, 37, 187-192). Optionally, further suitable promoter regions are obtained from regions upstream of the coding sequences of genomic DNA corresponding to cDNA sequences known in the art to be preferentially expressed in male reproductive structures. In certain embodiments such probe cDNAs are selected from the group consisting of the orchid pollen-tube specific cytochrome P450 gene (Nadeau et al., (1996) Plant Cell, 8, 213-239), the Bcp1 gene of *Arabidopsis* (Xu et al (1995) P.N.A.S., 92, 2106-2110) and the male-flower specific MFS14 gene of maize (Wright S Y et al., (1993) Plant J 3, 41-49). In further embodiments, further 5' promoter regions suitable for use in the chimeric genes of the invention are isolated and cloned by methods which are familiar to one skilled in the art. For example, novel transcripts expressed in male reproductive structures are identified by isolating RNA from tissues such as tassels, pollen tubes, anther or tapetum followed by differential screening by techniques such as differential display, PCR select cDNA subtraction and subtractive cDNA library construction. cDNA clones that are preferentially expressed in the male tissues and not in other parts of the plant such as the leaves, roots and stigma are isolated. The tissue specificity of expression is, optionally, confirmed by Northern blotting. The cDNA clones are used as probes for genomic library screening. 5' promoter regions and 3' untranslated DNA regions associated with tissue preferential expression are obtained from the genomic DNA clones and used in the construction of chimeric genes for preferential expression in male reproductive structures.

Further promoter regions useful in the chimeric genes of the invention include the regions upstream of the Osmads 13 gene of rice, the OSG gene of rice anther, and the YY2 gene of rice. Generally, promoter regions yielding high, early, sustained and preferential expression in male or female reproductive structures are selected as most suitable. Promoter regions may also further comprise chimeric combinations with each other and with further enhancer regions.

Chimeric genes may optionally comprise a region, immediately preceding the DNA sequence encoding the activating or inactivating enzyme which encodes a peptide sequence capable of targeting the said enzyme to subcellular organelles such as the chloroplast, peroxisome or mitochondria and the said targeting protein may have the sequence of (i) a chloroplast transit peptide or (ii) a chloroplast transit peptide-N-terminal portion of a chloroplast protein—chloroplast transit peptide. In certain embodiments the transit peptide sequence may be selected from the group consisting of the endogenous transit peptide sequences of the beta-subunit of *Nicotinia plumbaginifolia* mitochondrial ATP synthase, mitochondria-specific NADP-dependent isocitrate dehydrogenase, NADPH-binding subunit of respiratory chain complex I and yeast mitochondrial tryptophanyl-tRNA-synthetase (WO 6121513).

Polynucleotides for use in the present inventive method may comprise one or more chimeric genes which encode activating and inactivating enzymes. Optionally such polynucleotides comprise yet further genes and chimeric genes, such as a chimeric marker gene. A chimeric marker gene as used herein comprises a marker DNA under expression control of a promoter which is active in plant cells. The marker DNA encodes an RNA, protein or polypeptide which, when expressed in a plant, plant tissue or plant cell allows such plant material to be distinguished from plant material not expressing the marker DNA. Examples of marker genes are genes that provide a specific colour to a cell such as the A1 gene (Meyer et al. (1987) Nature 330, 667) or genes that render plant cells resistant to otherwise lethal selection with antibiotics (e.g. the aac(6') gene encoding resistance to gentamycin, WO 94/01560 or hygromycin phosphotransferase genes providing resistance to hygromycin) or herbicides (additional to the herbicide used to effect conditional male and/or female sterility in hybrid seed production) such as glyphosate (e.g EPSPS genes such as in U.S. Pat. No. 5,510,471 or WO 00/66748), phemnedipham (e.g. pmph gene U.S. Pat. No. 5,347,047; U.S. Pat. No. 5,543,306), phosphinothricin (PAT), bromoxynyl (e.g. genes described in U.S. Pat. No. 4,810,648) sulphonylureas (e.g. genes described in EP 0360750), dalapon (genes described in WO 99/48023) and cyanamide (genes described in WO 98/48023; WO 98/56238). In a preferred embodiment of the polynucleotide of the current invention which comprises an additional herbicide resistance gene as a marker gene, the said herbicide is a herbicide which is useful for weed control in the crop and, additionally, the herbicide resistance gene is expressed sufficiently to provide robust tolerance to field rates of the said herbicide. In a further preferred embodiment the additional herbicide is glyphosate and the herbicide resistance gene is an EPSP synthase. However the marker gene may be a gene that provides for positive selection wherein the marker gene encodes an enzyme which provides, in the context of a particular medium, the transformed plant cells with a positive metabolic advantage. U.S. Pat. No. 5,767,378 describes a number of suitable positive selection systems and genes.

Where the polynucleotide of the current invention comprises an additional herbicide resistance gene the herbicide may be exogenously applied to crop plants which are interplanted at a sufficient density to eliminate the production of non-hybrid seed originating from non-transgenic self-fertile parent plants. In a preferred embodiment the additional herbicide is glyphosate or an agronomically useful salt thereof and the said herbicide resistance marker gene is selected from amongst those glyphosate resistance conferring genes described in WO 00/66748.

Where a marker gene is present, means for the removal of said marker gene may also be provided. This is desirable where, for example, it is decided to combine traits. Polynucleotides which comprise marker genes may optionally comprise specific recognition sites for specific recombinases in positions which flank the marker gene and which allow the sequence to be 'kicked out'. Crossing of a plant carrying the so-flanked marker gene with a plant carrying a gene which encodes the corresponding specific recombinase results in progeny plants from which the marker is specifically excised. Examples of suitable such site-specific homologous recombination systems are the flp/frt system (Lyznik et al., (1996), Nucleic Acids Res. 24, 3784-3789) and the Cre/Lox system (Bayley, C. C. et al., (1992) PMB, 18, 353-361).

Polynucleotides used in the present inventive method may optionally comprise one or more translational enhancers located within the non translated regions 5' of the protein-encoding sequences. The skilled man is aware of the identity of such suitable translational enhancers—such as the Omega and Omega prime sequences derived from TMV and that derived from the tobacco etch virus, and how such translational enhancers can be introduced into the polynucleotide so as to provide for the desired result of increased protein expression. Further examples include translational enhancers derived from maize chlorotic mottle virus and alfalfa mosaic virus (Gallie et al., (1987) Nucl. Acids Res.; 15, 8693-8711; Skuzeski et al., (1990) PMB., 15, 65-79). To further optimise expression of proteins from chimeric genes and chimeric marker genes the said polynucleotides may also further comprise elements such as enhancers, scaffold attachment regions (SARS or MARS) and introns. Various intron sequences such as the maize adh1 intron 1 have been shown to enhance expression when included into the 5' untranslated region of genes and, optionally, are used in the chimeric genes of the current invention.

Plants which have been transformed according to the invention so as to exhibit the desired male/female sterility characteristics may also have been transformed with a polynucleotide which comprises regions encoding proteins capable of conferring upon plant material containing it at least one of the following agronomically desirable traits: resistance to insects, fungi, viruses, bacteria, nematodes, stress, dessication, and herbicides.

Herbicide resistance conferring genes may, for example, be selected from the group encoding the following proteins: glyphosate oxidase (GOX), EPSP synthase, hydroxyphenyl pyravate dioxygenase (HPPD), phosphinothricin acetyl transferase (PAT), glutathione S transferase (GST), cytochrome P450, Acetyl-CoA carboxylase (ACCase), Acetolactate synthase (ALS), protoporphyrinogen oxidase (PPO), dihydropteroate synthase, polyamine transport proteins, superoxide dismutase (SOD), bromoxynil nitrilase, phytoene desaturase (PDS), the product of the tfdA gene obtainable from *Alcaligenes eutrophus*, and known mutagenised or otherwise modified variants of the said proteins. The skilled man will recognise the need to choose such genes, and the promoters which drive their expression, carefully, having regard to the nature of the herbicide used to effect conditional sterility and the nature of the activating and inactivating enzymes. In the case that the polynucleotide provides for multiple herbicide resistance such herbicides may be selected from the group consisting of a dinitroaniline herbicide, triazolo-pyrimidines, a uracil, a phenylurea, a triketone, an isoxazole, an acetanilide, an oxadiazole, a triazinone, a sulfonanilide, an amide, an anilide, an isoxaflutole, a flurochloridone, a norflurazon, and a triazolinone type herbicide and the post-emergence herbicide is selected from the group consisting of glyphosate and salts thereof, glufosinate, asulam, bentazon, bialaphos, bromacil, sethoxydim or another cyclohexanedione, dicamba, fosamine, flupoxam, phenoxypropionate, quizalofop or another aryloxy-phenoxypropanoate, picloram, fluormetron, butafenacil, atrazine or another triazine, metribuzin, chlorimuron, chlorsulfuron, flumetsulam, halosulfuron, sulfometron, imazaquin, imazethapyr, isoxaben, imazamox, metosulam, pyrithrobac, rimsulfuron, bensulfuron, nicosulfuron, fomesafen, fluroglycofen, KIH9201, ET751, carfentrazone, mesotrione, sulcotrione, paraquat, diquat, bromoxynil and fenoxaprop.

In the case that the polynucleotide comprises sequences encoding insecticidal proteins, these proteins may be selected from the group consisting of crystal toxins derived from Bt, including secreted Bt toxins such as those known as "VIP"; protease inhibitors, lectins and Xenhorabdus/Photorhabdus toxins. The fungus resistance conferring genes may be selected from the group consisting of those encoding known AFPs, defensins, chitinases, glucanases, and Avr-Cf9. Particularly preferred insecticidal proteins are cryIAc, cryIAb, cry3A, Vip 1A, Vip 1B, Vip3A, Vip3B, cysteine protease inhibitors, and snowdrop lectin. In the case that the polynucleotide comprises bacterial resistance conferring genes these may be selected from the group consisting of those encoding cecropins and techyplesin and analogues thereof. Virus resistance conferring genes may be selected from the group consisting of those encoding virus coat proteins, movement proteins, viral replicases, and anti-sense and ribozyme sequences which are known to provide for virus resistance; whereas the stress, salt, and drought resistance conferring genes may be selected from those that encode Glutathione-S-transferase and peroxidase, the sequence which constitutes the known CBF1 regulatory sequence and genes which are known to provide for accumulation of trehalose.

Polynucleotides used in accordance with the present invention may have been "modified" to enhance expression of the protein encoding sequences comprised by them, in that mRNA instability motifs and/or fortuitous splice regions may have been removed, or crop preferred codons may have been used so that expression of the thus modified polynucleotide in a plant yields substantially similar protein having a substantially similar activity/function to that obtained by expression of the protein encoding regions of the unmodified polynucleotide in the organism in which such regions of the unmodified polynucleotide are endogenous. The degree of identity between the modified polynucleotide and a polynucleotide endogenously contained within the said plant and encoding substantially the same protein may be such as to prevent co-suppression between the modified and endogenous sequences. In this case the degree of identity between the sequences should preferably be less than about 70%. In addition the sequence around a translational start position may be modified such that it is "Kozack preferred". What is meant by this is well known to the skilled man.

The invention still further includes morphologically normal conditionally fertile whole plants which result from the crossing of plants which have been regenerated from material which has been transformed with the nucleic acid in accordance with the present invention and which therefore provides for such a trait. The invention also includes progeny of the resultant plants, their seeds and parts.

Plants of the invention may be selected from the group consisting of field crops, fruits and vegetables such as canola, sunflower, tobacco, sugar beet, cotton, maize, wheat, barley, rice, sorghum, mangel worzels, tomato, mango, peach, apple, pear, strawberry, banana, melon, potato, carrot, lettuce, cabbage, onion, *soya* spp, sugar cane, pea, field beans, poplar, grape, citrus, alfalfa, rye, oats, turf and forage grasses, flax and oilseed rape, and nut producing plants insofar as they are not already specifically mentioned, their progeny, seeds and parts.

Particularly preferred such plants include wheat, barley, oats, rice, maize, millet and sorghum.

The invention still further provides a preferred method of producing hybrid wheat seed which comprises the steps of
  (i) transforming plant material with one or more polynucleotides or vectors which comprise a herbicide inactivating gene expressed substantially only in the green tissue and a gene conferring male sterility conditional upon exogenous application of said herbicide;
  (ii) selecting the thus transformed material; and
  (iii) regenerating the thus selected material into morphologically normal conditionally male-sterile whole plants.
  (iv) breeding a homozygous conditionally male-sterile female parent line
  (v) transforming plant material with one or more polynucleotides or vectors which comprise a herbicide inactivating gene expressed substantially only in the green tissue and a gene conferring female sterility conditional upon exogenous application of the same herbicide as in (i);
  (vi) selecting the thus transformed material; and
  (vii) regenerating the thus selected material into morphologically normal conditionally female-sterile whole plants
  (viii) Breeding a homozygous conditionally female-sterile male parent line
  (ix) Interplanting said conditionally-sterile male and female parent lines at such a ratio as to ensure efficient pollination
  (x) Applying said herbicide to the interplanted parent lines at such a dose and stage in development as to minimise self-fertilisation
  (xi) Harvesting hybrid wheat seed from the interplanted parent plants The current invention also provides variants of the above method wherein the male parent is female sterile by any means, the female parent is male sterile by any means, male and female parent lines are conditionally sterile dependent upon the application of different herbicides both of which are applied, and the crop is other than wheat.

The present invention also includes a diagnostic kit comprising means for detecting the proteins, or DNA sequences encoding them, which are present in plants produced in accordance with the present inventive method and therefore suitable for identifying tissues or samples which contain these. The DNA sequences can be detected by PCR amplification as is known to the skilled man—based on primers which he can easily derive from the enzyme encoding sequences which are disclosed or mentioned in this application. The enzymes per se can be detected by, for example, the use of antibodies which have been raised against them for diagnostically distinguishing the antigenic regions which they contain.

In respect of the transformation of plant material, those skilled in the art will recognise that although particular types of target material (e.g. embryogenic cell suspension culture or de-differentiating immature embryos) and particular methods of transformation (e.g. using *Agrobacterium* or particle bombardment) are specified in the examples below, the present invention is not limited to these particular embodiments and such target materials and methods may be used interchangeably. Furthermore the term "plant cells" as used throughout this description of the invention can refer to isolated cells, including suspension cultures as well as to cells in an intact or partly intact tissue such as embryo, scutella, microspore, microspore-derived embryo or somatic cells from plant organs. Similarly, although the specific examples are limited to maize and wheat, the invention is equally applicable to a broad range of agricultural crops which can be transformed using suitable methods of plant cell transformation.

The present invention will be further apparent from the following non-limiting examples and sequences.

```
SEQ ID # 1 PRIMER
5'-AACTGCAGCTTTTTGGTTAGCGAATGC-3'

SEQ ID # 2 PRIMER
5'-CAGACTAGTTTTAGCTAATTTCTTTAAGTAAAAC-3'
```

General molecular biology methods are well established and are carried out accordingly. For the most part the following examples each comprise multiple exemplifications of the current invention. Where the term 'promoter region of a gene' is used this is taken to mean DNA sequences which comprise the promoter, sequences upstream of the promoter and also, optionally, all or part of the DNA sequence encoding the 5' untranslated leader region of the mRNA.

Example 1

Tobacco Plants that are Conditionally Female Sterile Dependent Upon Exogenous Application of Phosphinothricin DNA sequences encoding enzymes capable of hydrolysing N-acetyl L-phosphinothricin are well known in the literature and are, for example, derived from *Streptomyces viridichromogenes* (N-acetyl-L-phosphinothricylalanylalanine deacetylase) *E. coli* (arg E, N-acetyl ornithine deacetylase), *Stenotrophomonas* sp and *Comamonas acidovorans* and codon-optimised versions thereof are well known in the literature (e.g. EP531716, EP942965 and U.S. Pat. No. 6,555, 733). Such deacetylase DNA coding sequences are optionally also further improved for specific N-acetyl-1-phosphinothricin deacetylase activity by standard processes of mutation and selection (e.g. using a replica-plate assay to monitor for mutants exhibiting an increased growth inhibitory effect of N-acetyl phosphinothricin upon bacterial growth or in vitro colourimetric detection of the amine group of the phosphinothricin product) or by gene shuffling approaches employing similar selections. DNA deacetylase encoding sequences are, for example, obtained synthetically (which makes it easier to control which internal restriction enzyme sites are present and to create flanking sites to facilitate cloning). Flanking PCR-primer and synthetic DNA sequences are designed to place useful unique restriction sites for cloning. Preferably and in the case where the deacetylase coding sequence does not contain confounding internal sites, an Nco1 or Nde1 site is placed at the 5' end to facilitate the cloning of in-frame fusions with sequences added 5' to the ORF. Optionally, restriction sites are placed upstream of the ATG translational start site intervening sequences to conform to plant translational concensus sequences such as according to Kozak.

The 'delta S13 promoter' is a promoter region useful for obtaining preferential expression in female flower parts. This comprises a region −339 to −79 from the SLG13 promoter region fused to the −46 to +8 of the CMV 35S core promoter (Dzelkalns et al (1993) Plant Cell, 5, 833-863). This S13 promoter region is cloned into bluescript sk which plasmid is then further restricted and ligated with restriction fragments comprising the nos 3' transcriptional terminator region and one or other of the deacetylase coding sequences so as to create a 'delta S13-deacetylase-Nos terminator' expression cassette within a bluescript sk plasmid. This is then suitably restricted out as, for example, an EcoR1 fragment and, as such ligated back into a suitable site in a vector such as pBIN19 (Bevan (1984) Nucleic Acids Res.) or pCIB200 or pCIB2001 (WO 98/39462) for use for transformation using *Agrobacterium*. As described in WO 98/39462 pCIB200 contains the following unique polylinker restriction sites: EcoR1, Sst1, Kpn1, BglII, Xba1 and SalI. PCIB2001 contains an insertion in the polylinker which adds further unique restriction sites including MluI, BclI, AvrII, ApaI, HpaI and StuI. PCIB200 and pCIB2001 also provides selectable marker genes for plant and bacterial selection on kanamycin, left and right T-DNA borders, the RK2-derived trA function for mobilization between *E. coli* and other hosts and the oriT and oriV functions from RK2. Alternatively the binary vector pCIB10 which incorporates sequences from the wide host range plasmid pRK252 is used (Rothstein et al (1987) Gene 53, 153-161) or one of its derivatives which incorporates both kanamycin resistance genes and the hygromycin phosphotransferase gene such as pCIB715 is used (Gritz et al (1983) Gene 25, 179-188).

Alternatively the ~1.6 kb Stig1 promoter region (derived from EMBL accession X77823) is used. For example the coding region of the GUS gene in the stig1-GUS construct described by Goldman et al (1994) in EMBO J., 13, 2976-2984, is replaced with the DNA sequence encoding deacetylase enzyme and the resultant stig1-D-amino acid oxidase expression construct cloned into in a suitable vector such as pCIB200 at a position upstream of a 3' terminator sequence adjacent to a suitable marker gene and between T-DNA border sequences.

DNA sequences encoding the PAT gene from *Streptomyces viridichromogenes*, *Alcaligenes* and codon-optimised versions thereof are well known in the literature (EP257542 (*Streptomyces viridichromogenes* PAT enzyme), EP617121, EP297618, EP290986 (*Alcaligenes* PAT enzyme), EP275957 (optimised *Streptomyces* genes). A PAT gene suitable for use in tobacco is, for example, that described in accession number A02774. Such DNA coding sequences may, for example, be obtained synthetically (which makes it easier to control which internal restriction enzyme sites are present and to create flanking sites to facilitate cloning). Flanking PCR-primer and synthetic DNA sequences are designed to place useful unique restriction sites for cloning. Preferably and in the case where the PAT coding sequence does not contain confounding internal sites, an Nco1 or Nde1 site is placed at the 5' end to facilitate the cloning of in-frame fusions with sequences added 5' to the ORF. Optionally, restriction sites are placed upstream of the ATG translational start site intervening sequences to conform to plant translational concensus sequences such as according to Kozak.

In a further particular example the T-DNA insert within the binary vector is constructed according to FIG. 1. A construct comprising the DNA sequence encoding the deacetylase under operable control of the stig1 promoter region and also the DNA sequence (A02774) encoding L-phosphinothricin N-acetyl transferase (PAT) under operable control of the pea plastocyanin promoter region is cloned into a site between the LB/npt II gene and the RB of the T-DNA of the binary vector. In brief, the deacetylase encoding sequence is cloned into plasmid pFse4Stig1nos (described in WO9942598) behind the Stig1 promoter and in front of the nos terminator region (comprised within EMBL: ATU237588) as, for example, an NcoI/PstI fragment. The pea plastocyanin promoter region (derived from EMBL Accession number X16082) is obtained from pea genomic DNA by PCR and cloned in front of the PAT gene/nos terminator. The resultant PC-PAT-nos cassette is cloned behind the Stig1-seactylase-nos as, for example, a NotI fragment and this whole two gene construct is transferred to a binary vector (pVB6, a Bin19 derivative) as, for example, an FseI fragment.

In a further variant of the method the 5' terminus of the deacetylase gene, is cloned to place it immediately downstream of a region encoding a chloroplast transit peptide so that a chloroplast transit peptide/deacetylase fusion protein is encoded. The chloroplast transit peptide encoding sequence is derived from the *Arabidopsis* gene encoding the small subunit of EPSP synthase (Klee et al 1987 in Mol. Gen. Genet., 210, 437). Optionally this is modified to include an Sph1 site at the CTP processing site thereby replacing the Glu-Lys at this location with Cys-Met (SEQ in FIG. 9. of WO 92044490). Correspondingly, an SPh 1 site may be engineered at the N-terminus of the deacetylase coding sequence (converting the amino acid following the methionine to a leu). Alternatively the chloroplast transit peptide encoding sequence is derived from the Petunia gene encoding EPSP synthase (FIG. 11 of WO 92044490). Alternatively the chloroplast coding sequence is any one of a large number of possibilities including those derived from genes encoding the small subunit of Rubisco and including the so-called 'optimized' chimeric transit peptide sequence (FR 2673643). In all cases, rather than rely on subcloning, the whole desired DNA sequence encoding the chloroplast transit peptide/deacetylase polypeptide may simply be obtained synthetically. This sequence is cloned into a site downstream of the stig1 promoter region and upstream of an (e.g nos) terminator sequence within a suitable vector (e.g. replacing the GUS coding sequence in the vector containing the stig1→GUS construct described by Goldman et al (1994) in EMBO J., 13, 2976-2984). The whole gene expression construct, also including the PAT gene sequence under operable expression control of the plastocyanin promoter region is then cloned into a suitable site between the right and left borders of the T-DNA of a PVB6 vector.

Tobacco leaf discs are transformed with the recombinant binary vectors using methods similar to those described in Horsch et al (1985) Science, 227, 1229-1231. Many variations of the method may be used. The binary vector can be transformed into, for example, *Agrobacterium tumefaciens* strain LBA 4404 using the freeze thaw method of transformation. Tobacco transformation and whole plant regeneration is performed using *Nicotiana tabacum* var. *Samsun* according to protocols described by Draper et al (Plant Genetic Transformation, Blackwell Sci. Pub. 1989). Transformation events are selected on MS-media containing kanamycin or other suitable antibiotic. Alternatively selection is made on phosphinothricin. The presence of integrated transgenes is confirmed by PCR. Plants are regenerated and allowed to reach maturity and selfed on to produce seed. Northern and/or Western analysis is used to confirm tissue-specific expression of the deacetylase. The plants are self-fertile but have the condition of conditional female sterility. Seeds of the T1 generation are planted out. Once plantlets have grown to a sufficient size they are tested by PCR for the presence of transgene. PCR positive plants are transferred to the greenhouse. These plants are fully fertile in the absence of exogenously applied phosphinothricin. A subset of these (putatively) conditionally sterile plants are treated with DL-phosphiothricin or L phosphinothricin in various amounts and at varying growth stages. Such treatments are carried out on the T1 plants confirmed as PCR positive for the deacetylase gene, or, equally, such treatments are carried out directly on plants of the T0 generation (which are vegetatively cloned so that untreated clones of each event may be set aside for seed production). The observed fertility and vegetative tolerance to phosphinothricin is then used as a basis to select suitable plant lines exhibiting the clearest conditional sterility phenotype. For example, phosphinotricin is applied as a foliar spray, prior to or during the early stages of flower formation, at rates usually between 0.25 and 20 kg/ha. Undamaged appearing plants are selected and pollen from the treated plants is collected and viability is tested. Plants are obtained which appear relatively undamaged at treatment rates of up to 5 kg/ha phosphinothricin, which produce relatively little or no seed after treatment with phosphinothricin but which, nevertheless, under the same treatment conditions do produce near normal levels of viable pollen. Control plants are both transgenic and non-transgenic and are grown under identical conditions and under an identical regime of physical treatments except that treatment solutions are water or formulant. Further control plants are transgenic plants transformed with constructs, similar to those described above and which comprise a PAT gene under operable control of the plastocyanin promoter region but which do not comprise a deacetylase gene. The plastocyanin promoter region provides for preferential expression in the green tissues of the plant. It is found, unexpectedly, that such a promoter which, unlike for example, the 35S promoter region, is substantially expressed only in certain tissues of the plant and most notably in green tissues, does, nevertheless, when used in combination with the PAT gene provide for substantially complete reproductive tolerance to the herbicide DL PPT even at rates in excess of 2 kg/ha. Furthermore, in the absence of any suitable deacetylase being co-expressed in the floral tissues, the plastocyanin/PAT gene combination provides essentially complete reproductive tolerance with no significant loss of yield despite the PAT expression level being low or non-existent in many of the critical floral tissues when expressed under control of this promoter region.

Example 2

Tobacco Plants which are Conditionally Male Sterile Dependent Upon Exogenous Application of Phosphinothricin Deacetylase and PAT encoding sequences obtained are the same as in example 1.

The TA29 promoter region (Kriete et al (1996) Plant J., 9, 808-818) is cloned from tobacco genomic DNA by PCR using the primers 5'-AACTGCAGCTTTTTGGTTAGC-GAATGC-3' (SEQ ID #1) and 5'-CAGACTAGTTT-TAGCTAATTTCTTTAAGTAAAAAC-3' (SEQ ID #2). Through a series of restriction and subcloning steps the PCR fragment so obtained is placed upstream of the deacetylase coding sequence and a nos transcriptional terminator is added 3' of the coding region. The resultant TA29-deacetylase-nos terminator expression cassette is then cloned, obtained as a suitable restriction fragment and cloned into a binary vector as in Example 1.

Alternatively, the deacetylase coding sequence regions is cloned as a suitable restriction fragment (for example BamH1, Bgl/II where synthetic variants of coding sequences are designed so as to remove internal restriction sites) and fused to the CaMv 35S promoter and the nopaline synthase terminator regions by insertion into (for example) the BamH1 site of the binary vector pROK1 (Baulcombe et al (1986) Nature, 321, 446-449) in a sense configuration. The EcoR1-BamH1 fragment carrying the 35S promoter region is then excised and replaced with an EcoR1-BamH1 fragment from pAP30 (Kriete et al (1996) The Plant Journal 9, 809-818) carrying the TA29s promoter region fragment (−810 to +54). The resultant vectors can be termed pGKTA29_argE_deac, pGKTA29_*Streptomyces*_deac etc. according to the protein sequence encoded.

As in example 1, the DNA construct used for transformation comprises, in addition to the DNA sequence encoding a deacetylase under operable expression control of a tissue specific male floral promoter region such as 'TA 29', also a DNA sequence encoding a phosphinothricin N-acetyl transferase gene such as the 'PAT' gene under operable control of a promoter region such as that from the plastocyanin gene (in this case the region from the *Pisum sativum* plastocyanin gene).

Tobacco plant material is transformed, via *Agrobacterium*, with vector and transgenic plants are regenerated in a similar manner to that described in the previous example. The plants produced are self-fertile but are conditionally male sterile. Seeds of the T1 generation are planted out into soil. Once plantlets have grown to a sufficient size they are tested by PCR for the presence of transgene. PCR positive plants are transferred to the greenhouse. These plants are fully fertile in the absence of exogenously applied herbicide. A subset of these putatively conditionally sterile T1 plants, or, alternatively plantlets of T0 'events' (direct regenerants from transformation) are treated with phosphinothricin in various amounts and at varying growth stages. Where To plants are treated they are vegetatively cloned so that untreated siblings of the events are set aside for seed production. The observed vegetative tolerance to herbicide and then the subsequent observed male fertility is then used as a basis to select suitable plant lines exhibiting the clearest conditional sterility phenotype. For example, phosphinothricin is applied as a foliar spray, prior to or during the early stages of flower formation, at rates usually between 0.25 and 20 kg/ha.

In an alternative embodiment, the floral promoter region used is the 2.2 kb region (EMBO reference X57295) from upstream of the tap 1 gene from snapdragon (Spena et al, (1992), Theor. Appl. Genet., 84, 520-527).

Pollen from the treated plants is collected and viability is tested. Plants are obtained which shed no or relatively little pollen and/or pollen which is not viable. Pollen collected from some of the treated plants is tested and found to be malformed and non-viable. However, such male infertile plants remain female fertile and produce (hybrid) seed when pollinated with pollen collected from other, untreated non-transgenic or conditionally female-sterile tobacco plants. Control plants are both transgenic and non-transgenic and are grown under identical conditions and under an identical regime of physical treatments except that treatment solutions are either water or formulant.

Example 3

Chimeric Genes Preferentially Expressed in the Male Reproductive Structures of Cereals and Encoding Deactylase Enzymes Capable of Hydrolysing N-Acetyl L Phosphinothricin DNA sequences encoding deacetylase genes are obtained as described in example 1 and, optionally, are codon optimised for expression in cereals.

In one specific example, the anther specific SGB6 promoter region seq ID number 1 of U.S. Pat. No. 5,470,359 is used. pSGBNE1 containing a 3 kb genomic EcoR1-Nhe1 subcloned fragment from pSGB6g1 (U.S. Pat. No. 5,470,359) is further subcloned to place a 1558 bp ApaII/Xba1 fragment blunt cloned into bluescript ks at the SmaI site. Through further restriction and cloning steps this fragment is fused in frame upstream of either the deacetylase DNA coding sequences. A nos terminator is added 3' of the coding region to create, alternative, Bluescript sk plasmids, pBLB6_argE_deac, pBLB6_*Streptomyces*_deac comprising the alternative SGB6-deacetylase-nos expression cassettes.

In a similar set of examples the RA8 anther-specific promoter region from rice (EMBL/genbank accession AF042275; Jean J s et al (1999) PMB, 39, 35-44) is similarly also fused at a site in-frame and upstream of one or other of the DNA sequences encoding deacetylase and a nos 3' terminator to comprise alternative RA8-deactylase-nos expression cassettes in a series of bluescript sk vectors.

Optionally, chimeric genes of this example are, as in examples 1 and 2, combined into a single vector also comprising a chimeric PAT gene under operable expression control of a plastocyanin (or similar, predominantly green-tissue directing promoter region) prior to transformation into cereals.

Alternatively, the cereal tissue is cotransformed with separate vectors, one comprising the plastocyanin/PAT gene chimeric gene and the other the floral promoter/deacetylase chimeric gene and plants are regenerated and selected.

Example 4

Chimeric Genes Preferentially Expressed in the Female Reproductive Structures of Cereals and Encoding Enzymes Capable of Hydrolysing N-Acetyl L Phosphinothricin DNA sequences encoding deacetylase genes are obtained as described in example 1 and, optionally, are codon optimised for expression in cereals.

The genomic clone pSH64 was deposited under the terms of the Budapest treaty on 27 Feb. 1998 with NRRL and assigned the number NRRL B-21920. It was detected as a genomic clone hybridising to the silk-specific cDNA clone B200i4-2 (WO 98/39462). Chimeric genes which are expressed preferentially in female reproductive structures are constructed as follows. A bluescript ks-derived plasmid similar to pSH70 having an 'empty' expression cassette comprising, from 5' to 3', the B200i 5' promoter region consisting of nucleotides 1-3790 of SEQ D No 11 of WO 98/39462, a BamH1 site and the B200i 3' untranslated terminator region comprising nucleotides 4427-6397 of sequence ID No. 11 of WO 98/39462 is constructed as described in WO 98/39462. Using a partial BamH1 digestion or, alternatively by further subcloning, PCR and ligation steps alternative deacetylase coding sequences are ligated into the position at or adjacent to the BamH1 site such that they are immediately 3' of the B200i promoter region and 5' of the B200i terminator region. Accordingly, a series of bluescript vectors pBLB200_argE_deacetylase etc encoding the alternative B200i-D-amino acid oxidase-B200i expression cassettes are created.

Alternatively, as described in WO 98/39462, a Pst I/Nco I fragment of the 5' promoter region of the P19 gene is excised from the genomic clone X2-1 which was deposited under the terms of the Budapest treaty on 27 Feb. 1998 at NRRL and assigned accession number B-21919. The Nco I site at nucleotide 1088 of SEQ ID No 14 of WO 98/39462 corresponds with the ATG translational start of the P19 gene. Using appropriate subcloning, restriction, ligation and PCR steps this fragment is ligated to form a in-frame fusion with one or other of the DNA sequences encoding deacetylase and a nos terminator sequence is added 3' of the coding sequence. Accordingly, a series of bluescript vectors encoding the alternative P19-deacetylase-nos expression cassettes are created. Alternatively, using similar standard methods, similar plasmids are obtained having the 5' promoter region (comprising some or all of nucleotides 1-3987 of SEQ ID No 2 of WO 98/39462) of the P26 gene in place of the P19 promoter region. The genomic P26-A4 clone, pCIB10302 deposited under the terms of the Budapest Treaty on Jan. 21, 1997 with the Agricultural Research Service patent culture collection, (NRRL) accession number NRRL B-21655 is subcloned as described in WO 98/39462. Accordingly, a series of bluescript vectors pBLP26_*Streptomyces*_deac etc. encoding the alternative P19-deacetylase-nos expression cassettes are created.

Example 5

A Pair of Complementary Constructs Useful in a Method to Provide (a) a Female Inbred Parental Line which is Conditionally Male-Sterile Dependent Upon the Application of DL Phosphinothricin and (b) a Complementary Male Inbred Parental Line Which is Conditionally Female Sterile Dependent Upon the Application of DL Phosphinothricin The first DNA construct suitable for providing a female inbred parental cereal or rice plant line which is conditionally male-sterile dependent upon the application of DL phosphinothricin comprises three genes A), B) and C). A) consists of a DNA sequence encoding a PAT enzyme capable of N-acetylating L-phosphinothricin under operable control of the ~1 kb promoter region from the barley plastocyanin gene (EMBL: Z28347) and a suitable terminator region such as that from the nos or 35S gene, B) consists of a PAT encoding sequence similar to the first but this time under operable control of a tissue specific female floral promoter region (such as P19 or P26) plus a suitable terminator and C) consists of a suitable deacetylase encoding sequence as described in example 1 under operable control of a tissue specific male floral promoter region (such as SGB6 or RA8) and a suitable terminator region. This construct is assembled using methods which are standard in the art and informed by the previous examples.

The second DNA construct suitable for providing a male inbred parental cereal or rice plant line which is conditionally female-sterile dependent upon the application of DL phosphinothricin comprises three genes A), D) and F). A) consists of a DNA sequence encoding a PAT enzyme capable of N-acetylating L-phosphinothricin under operable control of the promoter region from the barley plastocyanin gene and a suitable terminator region such as that from the nos or 35S gene, D) consists of a PAT sequence similar to the first but this time under operable control of the same tissue specific male floral promoter region (such as SGB6 or RA8) as used in the first construct to drive expression of the deacetylase plus a is suitable terminator and F) consists of a suitable deacetylase encoding sequence as described in examples 1 under operable control of the same tissue specific female floral promoter region (such as P19 or P26) as used to drive expression of PAT in the first construct and a suitable terminator region. This construct is assembled using methods which are standard in the art and informed by the previous examples.

A pair of DNA constructs of this example contain, for example, the following elements Construct 1

A=Barley plastocyanin promoter region→PAT encoding sequence, Nos terminator;

B=P26 promoter region→PAT encoding sequence, 35S terminator;

C=RA8 promoter region→deacetylase encoding sequence, Nos terminator

Construct 2

A=Barley plastocyanin promoter region→PAT encoding sequence, Nos terminator;

D=RA8 promoter region→PAT encoding sequence, 35S terminator;

E=P26 promoter region→deacetylase encoding sequence, Nos terminator

Example 6

Polynucleotide Vectors for Transformation of Wheat

The previous examples describe the construction of various chimeric genes in expression cassettes which are usually cloned into bluescript sk. Optionally these vectors are prepared in bulk for direct DNA transformation for use with a co-bombarded selectable marker such as pSOG35 (DHFR/ methotrexate) or pUbi-Hyg (hygromycin phosphotransferase/hygromycin) as described in WO 98/39462. Preferably, after bulk preparation, the vectors are linearised using a suitable restriction enzyme to remove the ampicillin resistance gene of bluescript.

Optionally, rather than use co-bombardment the said bluescript vectors are further engineered by standard methods so that they further comprise a plant selectable marker gene such as kanamycin resistance, hygromycin resistance, methotrexate resistance or glyphosate resistance gene and are used directly. In some of the foregoing examples a PAT gene is integral to the design of the vector and, in these cases, DL phosphinothricin may optionally be used for selection at some stage after transformation.

Alternatively, expression cassettes are excised within a suitable restriction fragment and cloned into pIGPD9 derived vectors (described in FIG. 12 of WO 00/66748). The use of this vector for transformation avoids transfer of antibiotic marker genes to the plant since its maintenance in bacteria relies on complementation of an auxotrophic his B *E. coli* mutant. The vector comprises a gene expressing IGPD (the hisB product) and is further engineered to comprise a plant selectable marker gene such as an EPSPS gene cloned into the Xma I site as, for example, in pZEN16i and pZEN18i of WO 00/66748. Alternatively a marker gene which provides positive selection on mannose or xylose is used (U.S. Pat. No. 5,767,378).

Large-scale DNA preparations for use in plant transformation are obtained using the Maxi-prep procedure (Qiagen) using protocols supplied by the manufacturer.

Example 7

Transformation/Regeneration of Wheat with Polynucleotides Comprising Chimeric Genes Providing for Tissue Specific Expression of PAT and of N-Acetyl L Phosphinothricin Deacetylase In one example, immature embryos (0.75-1.0 mm in length) of genotype UC703 are plated on MS medium containing 3 mg/l 2,4-D and 3% sucrose. After approximately 4 h the embryos are plated onto MS medium containing 15% maltose, 3% sucrose and 3 mg/l 2,4-D overlaid with a filter paper supported slab of agarose containing the same components. The embryos are allowed to plasmolyze for 2-3 h before bombardment.

DNA prepared as described in the foregoing examples is precipitated onto micrometer size gold particles using standard procedures. Four target plates with 16 embryos per target are shot twice with a DuPont Biolistics helium device using a burst pressure of 1100 psi. Plates are shot with an 80 mesh screen in place between the carrier stage and the target. After bombardment targets are placed in the dark at 25 C for 24 h before the slabs with the embryos are laid onto plates of MS medium containing 3% sucrose and 3 mg/l 2,4-D. The individual embryos are removed from the slabs and placed directly on fresh medium of the same composition after another 48 h. Where methotrexate is the selecting agent, approximately 6 weeks after gene delivery the tissue is placed on MS medium with 3 mg/l 2,4-D, 3% sucrose and 0.2 mg/l of methotrexate for a 3 week period. The tissue is then placed on regeneration medium comprised of MS medium containing 1 mg/l zeatin riboside and 1 mg/l methotrexate. After 2 weeks regenerating plantlets are placed in sterile containers with half-strength MS medium containing 2% sucrose, 1 mg/l napthylacetic acid and 4 mg/l methotrexate. Similar procedures are adapted according to the use of other selection agents.

In particular variants of the example the vectors comprising chimeric genes preferentially expressed in male reproductive structures are co-bombarded with alternative selectable marker genes. Thus, for example, DNA of plasmids comprising a chimeric gene wherein deacetylase is expressed under operable control of the RA8 promoter region is prepared and coated onto gold particles along with pUbiHyg (a plasmid encoding hygromycin phosphotransferase under operable control of the maize polyubiquitin promoter). In this case transformation and regeneration is carried out as described above except that, following bombardment, the regeneration media contain increasing concentrations of hygromycin between 2 and 20 mg/l.

In a further example wheat is transformed with plasmids expressing a glyphosate-resistant EPSP synthase and is selected using glyphosate and regenerated as described in example 15 of WO 00/66748

DNA is extracted from leaf tissues of plants derived from transformation and PCR is carried out in order to detect the presence of PAT gene, optionally any additional selectable marker gene and the gene encoding deacetylase. PCR positive plants are propagated. During flowering, pistils and anthers are collected and RNA is prepared. DNA expression is confirmed by Northern analysis. In addition, deacetylase genes are expressed using pET vectors in *E. coli* and part purified. The protein bands of the expressed protein is cut out of an SDS gel and used to generate polyclonal antibodies. These antibodies are used to detect expression in flower tissues and other tissues by Western analysis.

Example 8

A Method of Efficiently Producing Hybrid Cereal Crops Wherein DL Phosphinothricin is Applied Both for Weed Control and at the Same Time as the Chemical Hybridising Agent and Wherein the F1 Hybrid Generation of Plants Resulting from the So-Produced Hybrid Seed is Both Vegetatively and Reproductively Substantially Tolerant to the application of DL Phosphinothricin Chemical hybridising agents are expensive and not always effective. It would be desirable to use a relatively cheap substance such as a commercial herbicide as a chemical hybridising agent. This would also achieve further efficiency since weed control could be combined with chemical hybridisation. However there are a number of problems to overcome in order that this proposition be realised. Firstly, male and female parental lines need be established which are tolerant to the herbicide in question. Furthermore, in order to achieve the desired 'conditional' fertility in response to application of the herbicide the two parental lines need to be engineered in such a way that tolerance to the said herbicide does not extend to all tissues but, rather, is expressed in a tissue specific manner so that each one of the required floral tissues remains selectively susceptible. Thus, in one line (the female parent line), the bulk of the plant plus the female tissue must be rendered tolerant whilst some critical part of the male floral tissue must remain susceptible to the application whereas in the other (the male parent line), the converse is needed with only some critical part of the female gamete forming tissue remaining susceptible. Even given that this can be achieved there remains a further problem to overcome in respect of the hybrid seed and F1 generation. Given that this generation of the crop would, according to the above-outlined scheme, necessarily, contain at least two genes capable of conferring resistance to the herbicide it would be desirable that this same herbicide could also be available as an option for use as a selective weed control agent in the F1 hybrid crop. However, it is difficult to conceive of a combination of herbicides, tissue specific promoter regions and tolerance genes that would permit this use of the same herbicide in the F1 generation as was used as the hybridisation agent in the process of hybrid seed production. It would be likely that the hybrid crop would display vegetative tolerance but little or no grain yield after herbicide application to the F1 generation. No such hybrid crop production systems currently exists. To take the conceptual example of how, for example, glyphosate might be used as combined hybridisation agent and F1 crop selective herbicide may help to make the inherent difficulty plain. For the herbicide glyphosate the usual mechanism of resistance is the expression of a resistant form of EPSP synthase. It is difficult to identify a promoter region or combination of promoter regions that would permit sufficient expression of a R-EPSPS in all tissues and at all times other than, say, at a critical stage in the development of stamens or stigmas. The most straightforward way around this would be to use an antisense or similar approach wherein expression of the R-EPSPS is driven by a tissue non-specific/constitutive promoter and only locally and transiently suppressed in, for example, the stamens due to expression of an antisense EPSPS gene (see for example WO 9946396). However, in that case the suppression of expression in the stamen (or stigma) would be driven by a dominant gene. It is clear that, for any such mechanism, the application of the herbicide to the F1 generation would result in a sterile non-yielding crop due to the additive effects of both the dominant male and female conditional sterility genes being present in the F1 hybrid generation.

The current example along with the constructs provided in the previous examples provides a method of overcoming the problem of enabling the use of the relatively cheap commercial herbicide, DL phosphinothricin, as both weed control and hybridising agent in the production of hybrid cereals and which method, furthermore, provides resultant hybrid cereals in which DL phosphinothricin (or L phosphinothricin) can be safely used for weed control without substantial loss of yield. As a yet further benefit, selfed seed from the F1 generation which may later arise as volunteers in subsequent crops will be easier to manage since they, themselves, will generally be sterile if sprayed with controlling amounts of DL phosphinothricin. The same will hold for the progeny of pollen outcrossing from the F1 plants to weeds (e.g red rice) or other cereals.

In the method of producing hybrid crops of the current example the PAT gene is used to provide tolerance to the herbicide phosphinothricin which is used as the hybridisation agent. The PAT gene which converts L-phosphinothricin to N-acetyl L-phosphinothricin is, of course, already well known and is used commercially to provide tolerance to DL phosphinothricin in crops. However, there are a number of critical feature in relation to the expression of the PAT gene which characterise the method of the current example.

Firstly, the PAT gene is expressed under operable control of a plastocyanin promoter region so that it is expressed substantially only in the green tissues of the plant. Surprisingly, it is found experimentally that having the PAT gene so-expressed provides wheat plants that are substantially reproductively tolerant to the application of DL phosphinothricin at rates up of at least 2 kg/ha. Thus reproductive tolerance to phosphinothricin does not require that the PAT resistance gene be substantially expressed in the gamete-forming tissues themselves. Thus a critical feature of the constructs described in the foregoing examples which are used to provide the plants of the current example is that the PAT gene which provides the resistance trait is expressed under operable control of a promoter region which provides for expression in substantially only the green tissues. A characteristic of such a useful promoter region is that it should express PAT in such a way that it protects adequately all the non-green floral tissues from foliarly applied DL phosphinothricin whilst, at the same time, providing only a minimal level of PAT expression in the floral tissue itself and especially low in those parts targeted for conditional sterility. With PAT expressed under operable control of the barley plastocyanin promoter region this condition appears to be met since substantially all of the L-phosphinothricin which is sprayed enters via the leaves is intercepted and converted to non-phytotoxic N-acetyl-L-phosphinothricin before it translocated to developing floral tissues. Thus, in the method of the current example, the herbicide, L phosphinothricin which causes the tissue selective sterility effects in the parental lines is only generated transiently and locally from phloem mobile non-phytotoxic N-acetyl-L phosphinothricin via the action of a deacetylase enzyme.

A second feature of the expression of PAT characterising the method of the current example for making hybrid crops is that the conditionally sterile male and female parent lines comprise the constructs 1 or 2 as described in example 5. By exactly matching the floral control elements driving expression of PAT to those elements which drive expression of deacetylase in the complementary pair of constructs (example 5) it is ensured that, in the F1 hybrid, the transient burst of L-phosphinothricin in the target floral tissue is rapidly neutralised by a corresponding burst of PAT expression at the same time and in the same local tissue. Thus application of the herbicide induces no significant sterility effect in the hybrid upon either the male or female gamete forming tissue. However, in further generations, the florally corresponding PAT and D-amino acid oxidase of the hybrid will segregate apart and thus, once again, the resulting plants will be male or female sterile upon application of controlling amounts of DL phosphinothricin.

In the method of the current example, constructs described in example 5 are transformed into wheat as described in the foregoing examples or (using standard superbinary vector methods into rice) and transformant plants are selected and regenerated into plantlets. T0 transformant events are selected (using clonal propagation of tillers to maintain untreated lines) and suitable events for breeding on as, alternatively, male inbred parental lines which are conditionally female sterile dependent upon the application of DL phosphinothricin or female inbred lines which are conditionally male sterile dependent upon the application of DL phosphinotricin are selected using methods essentially as described in examples 1 and 2. The best lines exhibit the best herbicide tolerance, minimum yield loss, cleanest conditional sterility phenotype etc. The alternative male parent and female parent lines are selected and, optionally, backcrossed into suitable elite lines for a number of generations. The genetic inserts in these finally selected events are fully characterized as are the genetics of the inheritance of the conditional fertility and herbicide resistance traits and the characteristics of expressed gene products.

The, thus selected, female and male parental lines are then interplanted together in suitable ratios in a field and sprayed with DL phosphinothricin at a suitable rate between 0.05 and 10 kg/ha and timing up to the period of early flowering selected to optimise the production of hybrid seed. The seed thus produced have the advantage that they will give rise to plants which not only benefit from hybrid vigour but which are also tolerant to the herbicide formulations containing DL phosphinithricin which may thus be used for selective weed control in the crop. The hybrid seed also have the advantage that the herbicide tolerance trait that they express will be only incompletely passed onto future selfed generations or outcrossed into related weeds. Thus, for example, the hybrid rice resulting from this invention can be grown using DL phosphinothricin as weed control agent without significant loss of yield. However future generations of red rice plants which arise as the progeny of pollen from the hybrid rice outcrossing with red rice female parents will be vegetatively tolerant to treatment with DL phosphinothricin but have reduced self-fertility (owing to the expression of a deacetylase in the floral tissue) and thus produce little grain. Similarly, second generation volunteers of rice or wheat which arise from the hybrid crop will, for the most part, not produce grain after spraying with DL phosphinothricin.

The invention claimed is:

1. A method of producing male sterile plants, comprising the steps of transforming plant material with a polynucleotide which encodes a first enzyme which is capable of N-acetylating L-phosphinothricin and a second enzyme which is capable of removing the acetyl group from the N-acetyl L-phosphinothricin to yield L-phosphinothricin, and regenerating the thus transformed material into a plant, wherein the first enzyme is expressed in the green tissues of the plant and additionally expressed from a female-specific floral promoter so that the enzyme is present only in green tissues and in reproductive tissues other than those reproductive tissues in which male gametes are rendered non-functional, and wherein L-phosphinothricin herbicide is applied to the plant foliarly up to the time of male gamete formation and/or maturation, so that the plant is substantially undamaged by the application of herbicide, and wherein the second enzyme is expressed preferentially in male reproductive structures so that the selective local regeneration of L-phosphinothricin in these tissues prevents the formation of the said male gametes, or otherwise renders them non-functional.

2. A method according to claim 1, wherein the first enzyme is a phosphinothricin acetyl transferase (PAT) and the second enzyme is a deacetylase.

3. A method according to claim 1, wherein the L-phosphinothricin is applied in mixture along with D-phosphinothricin and/or at least one further compound selected from the group consisting of: safeners, gametocides, glutathione S transferase inducers, Cytochrome P-450 inducers or inhibitors, herbicides, fertilizers, nematocides, synergists, insecticides, fungicides, hormones and plant growth regulators.

4. A method according to claim 2, wherein the PAT enzyme is under expression control of a plastocyanin promoter.

* * * * *